(12) United States Patent
Nozaki et al.

(10) Patent No.: US 6,613,034 B2
(45) Date of Patent: Sep. 2, 2003

(54) HIGHLY DURABLE SANITARY PANTY

(75) Inventors: Satoshi Nozaki, Kagawa (JP); Mitsuhiro Wada, Kagawa (JP); Ayami Suga, Kagawa (JP)

(73) Assignee: Uni-Charm Corporation, Kawanoe (JP)

(*) Notice: Subject to any disclaimer, the term of this patent is extended or adjusted under 35 U.S.C. 154(b) by 0 days.

(21) Appl. No.: 09/799,421

(22) Filed: Mar. 5, 2001

(65) Prior Publication Data

US 2001/0020158 A1 Sep. 6, 2001

(30) Foreign Application Priority Data

Mar. 6, 2000 (JP) ........................................ 2000-060267

(51) Int. Cl.[7] ................................................ A61F 13/15
(52) U.S. Cl. .................................. 604/396; 604/385.22
(58) Field of Search .............................. 604/396, 398, 604/385.01, 385.22; 2/400, 406, 403, 405, 238, 338

(56) References Cited

U.S. PATENT DOCUMENTS

| | | | | |
|---|---|---|---|---|
| 2,058,970 A | * | 10/1936 | Flesh | 128/159 |
| 2,250,506 A | * | 7/1941 | Snyder | 2/224 |
| 2,462,195 A | * | 2/1949 | Jacobson | 2/224 |
| 2,596,127 A | * | 5/1952 | Carmean | 128/288 |
| 2,632,177 A | * | 3/1953 | Bigger | 2/224 |
| 2,977,957 A | * | 4/1961 | Clyne | 128/291 |
| 4,476,895 A | * | 10/1984 | Shibusawa | 128/546 |
| 4,628,930 A | * | 12/1986 | Williams | 128/379 |
| 5,131,100 A | * | 7/1992 | Atwater et al. | 2/405 |
| 5,239,706 A | * | 8/1993 | Stevenson | 2/408 |
| 5,291,617 A | * | 3/1994 | Moretz et al. | 2/400 |
| 5,435,014 A | * | 7/1995 | Moretz et al. | 2/403 |
| 5,528,775 A | * | 6/1996 | Marenda | 2/406 |
| 5,546,607 A | * | 8/1996 | Roberts | 2/406 |
| 5,593,400 A | * | 1/1997 | O'Leary | 604/385.2 |
| 5,700,256 A | * | 12/1997 | Yamamoto et al. | 604/397 |
| 5,701,608 A | * | 12/1997 | Kohn | 2/406 |
| 5,855,573 A | * | 1/1999 | Johansson | 604/385.2 |
| 5,858,885 A | * | 1/1999 | Hamilton et al. | 442/184 |

FOREIGN PATENT DOCUMENTS

| | | |
|---|---|---|
| JP | 9-504194 | 4/1997 |
| WO | WO-95/09594 | 4/1995 |

* cited by examiner

*Primary Examiner*—Weilun Lo
*Assistant Examiner*—Jacqueline F Stephens
(74) *Attorney, Agent, or Firm*—Darby & Darby (57) ABSTRACT

Provided is a sanitary panty including a front part, a back part, a crotch part positioned between the front part and the back part, and a waist portion formed by upper end portions of the front part and the back part. A pair of leg openings are formed below joining portions between side edges of the front part and side edges of the back part. A suspending member is formed with a stretchable material and extended from the front part, the crotch part and the back part. The suspending member is gradually reduced a width from the waist portion to the crotch part in the back part. An extension cloth extends from both sides of the suspending member to the leg openings at least in the crotch part.

14 Claims, 5 Drawing Sheets

HIGHLY DURABLE SANITARY PANTY

BACKGROUND OF THE INVENTION

1. Field of the Invention

The present invention relates to a sanitary panty with superior wear ability and wearing comfort.

2. Description of the Related Art

A sanitary panty typically has a structure, in which a waterproof sheet is sewn on inner side of crotch cloth portion of a general panty for preventing leakage and external extruding of menstrual blood. Since the sanitary panty is required to prevent side leakage or so forth due to motion of body or variation of attitude in sporting and sleeping, various measures have been taken in sewing position and dimension of the waterproof sheet. Various measures have also been taken for overall structure of the sanitary panty to provide superior wear ability and wearing comfort.

Figure 5A:
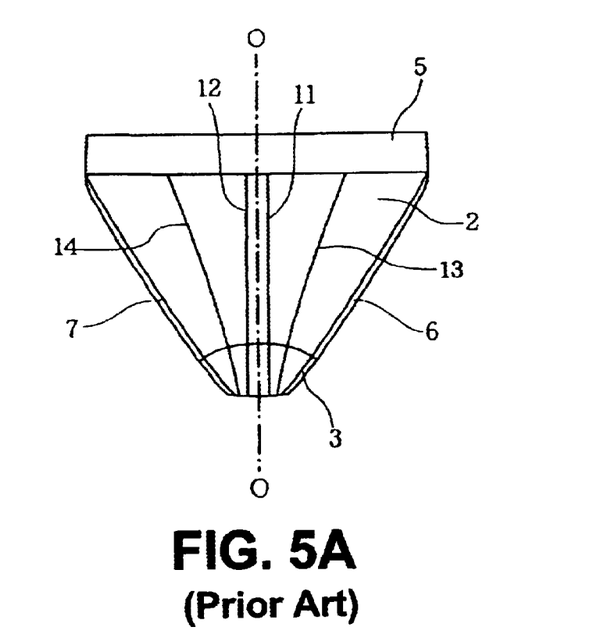
FIG. 5A is a front elevation and FIG. 5B is a back elevation.
Figure 5B:
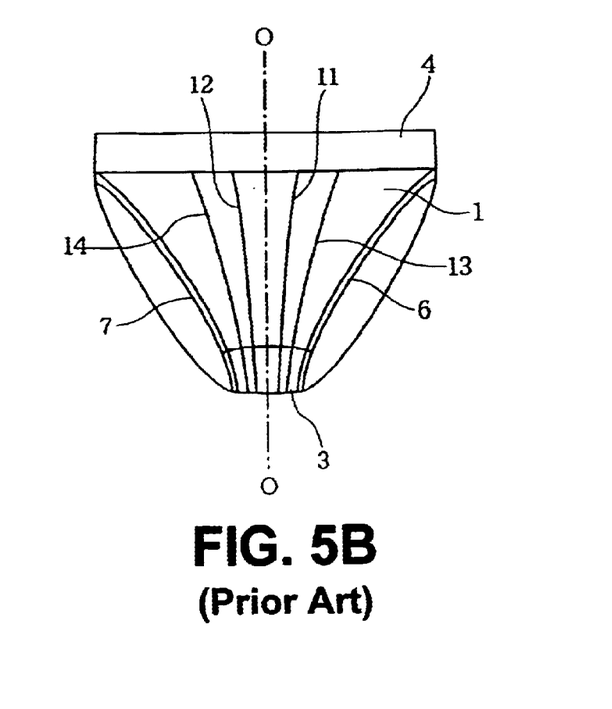

Japanese Unexamined Patent Publication (Kohyo) No. Heisei 9-504194 (corresponding to British Patent No. 2 282 522) discloses a sanitary panty taken the measure as set forth above. FIGS. 5A and 5B are front elevation and back elevation of typical one of the sanitary panties disclosed in the above-identified publication.

The sanitary panty illustrated in FIGS. 5A and 5B includes a front part 1, a back part 2 and an intermediate crotch part 3. The sanitary panty is also provided with waist elastic which has the form of elastic ribbons 4 and 5 mounted along the front part 1 and the back part 2 of the waist edge, and a pair of leg openings 6 and 7 which are formed by connecting the elastic ribbons 4 and 5.

The sanitary panty is also provided with two elastic threads 11 and 12 which extend between the respective elastic ribbons 4 and 5 of the front and back parts 1 and 2, symmetrically in relation to a center line O—O extending in the longitudinal direction of the panty. In the front part 1, the elastic threads 11 and 12 extend divergently from the waist edge of the front part 1 to the crotch part 3. In the back part 2, the elastic threads 11 and 12 extend close together and parallel with the longitudinal panty line from the waist edge of the back part 2 to the crotch part 3.

Also, the sanitary panty includes elastic threads 13 and 14 which lie laterally outsides of the threads 11 and 12 to extend across the front part 1, the crotch part 3 and the back part 2 and be connected to the elastic ribbons 4 and 5. The elastic threads 13 and 14 are mutually convergent in the crotch part 3 of the sanitary panty and are mutually divergent toward the waist edge of the front part 1 and the back part 2 of the sanitary panty along the center line O—O.

In the sanitary panty shown in FIG. 5, the crotch part 3 is pulled upwardly by means of four elastic threads 11, 12, 13 and 14 for urging a sanitary napkin to the wearer's body at the crotch part. Thus, lateral disposition of the sanitary napkin can be prevented to prevent leakage and external extruding of the menstrual blood from the sanitary napkin.

In the conventional sanitary panty as set forth above, four elastic threads 11, 12, 13 and 14 are employed as an elastic member for pulling the crotch part 3 upwardly. Accordingly, in the lower portion of the front part 1 and the lower portion of the rear part 2, the thin elastic threads 11, 12, 13 and 14 locally contact with the skin of the wearer to significantly degrade wearing comfort.

On the other hand, the elastic threads 11, 12, 13 and 14 having function for pulling up the sanitary napkin for firmly fitting the latter to the wearer are connected to the elastic ribbons 4 and 5 at respectively one point. As a result, upon firmly fitted to a waist portion of the wearer by elastic force of the elastic ribbons 4 and 5, the side portions of the elastic ribbons mainly serve for preventing the sanitary panty from slacking down. The elastic ribbons 4 and 5 at abdominal region and back region (hit side) tends to have slightly lower tightening in fitting on the wearer's body.

That is, when the elastic threads 11, 12, 13 and 14 are connected to the elastic ribbons 4 and 5 at respective one point, the tension force of the elastic threads is locally exerted to the elastic ribbons 4 and 5 to possibly curve or droop the elastic ribbons 4 and 5 downwardly toward the crotch part 3 at the portions respectively contacting with the abdominal region and the back region (hip side) to result in slacking down of the sanitary panty. Then, the tension force of the elastic threads 11, 12, 13 and 14 along the center line O—O can be lowered. As a result, the biasing force to be exerted to the sanitary napkin to the crotch part of the wearer's body is lowered to increase possibility of occurrence of disposition of the sanitary napkin.

Also, since the conventional sanitary panty has a structure, in which the thin elastic threads 11, 12, 13 and 14 are fitted to cloth forming the front part 1 and the back part 2, the crease can be easily formed in the cloth at the portions where the elastic threads 11, 12, 13 and 14 are provided. Also, since the sanitary panty has a structure to easily get loose of the elastic threads 11, 12, 13 and 14 in the worn condition as set forth above, the crease can be formed in the cloth at the portions of the elastic threads even if the sanitary panty is firmly pulled up in wearing.

The crease may provide uncomfortable feeling for the wearer's skin in the abdominal portion or the back portion (hip portion) of the body to significantly degrade wearing comfort. Also, the crease may influence for slacks, pants or the like to make the crease visible externally.

SUMMARY OF THE INVENTION

An object of the present invention is to provide a sanitary panty which can prevent an elastic member serving for pulling up a sanitary napkin fitted on crotch part, from slacking and whereby can prevent the sanitary napkin from causing side disposition, hardly slacking down, and hardly forming the crease.

According to one aspect of the present invention, a sanitary panty may comprise:

a front part;

a back part;

a crotch part positioned between the front part and the back part;

a waist portion formed by upper end portions of the front part and the back part;

a pair of leg openings formed below joining portions between side edges of the front part and side edges of the back part;

a suspending member formed with a stretchable material and extending from the front part, the crotch part and the back part, the suspending member being gradually reduced a width from the waist portion to the crotch part in the back part; and an extension cloth extending from both sides of the suspending member to the leg openings at least in the crotch part.

In the preferred construction, in the crotch part, a width W1 of the suspending member is greater than or equal to 10 mm and less than or equal to 40 mm, and more preferably greater than or equal to 20 mm and less than or equal to 40 mm.

A narrow width portion in which a width falls within a range of the width W1, may be provided in the suspending member from the crotch part to a given height position of the back part.

Both side portions of the suspending member located in the front part may be connected to both side portions of the suspending member located in the back part to form the waist portion with the stretchable material forming the suspending member.

The extension cloth may be provided from the crotch part to the back part to form a hip receiving portion.

The extension cloth may be further extended from both sides of the suspending member in the front part, both end portions of the extension cloth located in the front part and both end portions of the extension cloth located in the back part are connected to form the entire circumference of the leg openings with a material of the extension cloth.

The front part may be formed only by the material forming the suspending member.

The material forming the extension cloth may be not stretchable or has smaller stretching amount than that of the suspending member when the same tension force is applied.

The material forming the extension cloth may have stretchability and may have an elastic stress smaller than that of the stretchable material forming the suspending member, when the extension cloth and the suspending member are stretched in the same amount.

A waterproof sheet having stretchability and moisture permeability may be fitted inside of the crotch part or a portion extending from the crotch part to the back part.

The sanitary panty according to the present invention is provided with the suspending member formed with the stretchable material over the crotch part to the waist portion of the back part. The suspending member increases a width gradually from the crotch part to reach the waist portion. Thus, in the waist portion, the elastic stress of the suspending member will never be locally exerted but can be distributed over the entire length of the waist portion.

Accordingly, the sanitary panty is hardly slacked down to permit firm fitting of the entire back part to the back and hit portion of the wearer's body. Accordingly, the suspending member will never be relaxed to assure firm fitting of the sanitary napkin to successfully prevent side disposition. Also, the crease is hardly formed in the back part. Also, since the extension cloths having low stretchability are provided on both sides of the suspending member, the hip portion can be comfortably supported by the extension cloths like a normal panty.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings:

FIGS. 1A and 1B show the first embodiment of a sanitary panty according to the present invention, wherein

FIGS. 3A and 3B show the second embodiment of a sanitary panty according to the present invention, wherein

FIGS. 5A and 5B show the conventional sanitary panty, wherein

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific detailed. In the other instance, well known structure are not shown in detail in order to avoid unnecessary obscurity of the present invention.

Figure 1A:
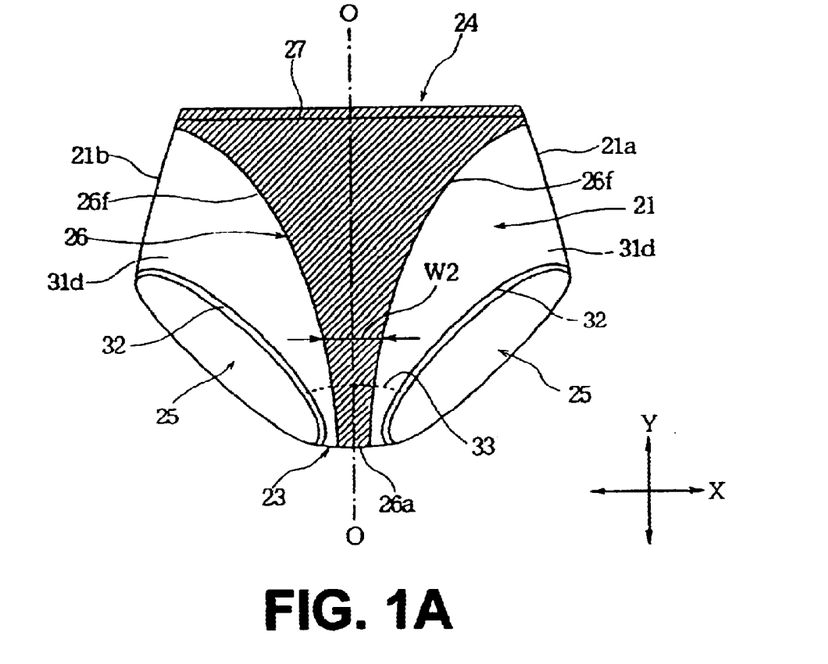
FIG. 1A is a front elevation and FIG. 1B is a back elevation.
Figure 1B:
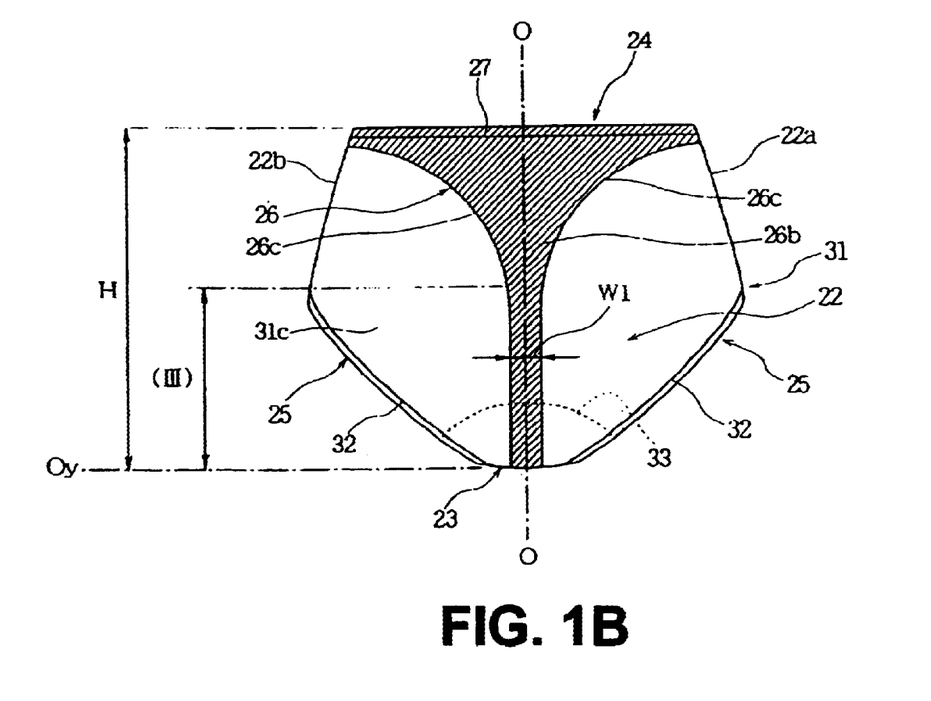
Figure 2:
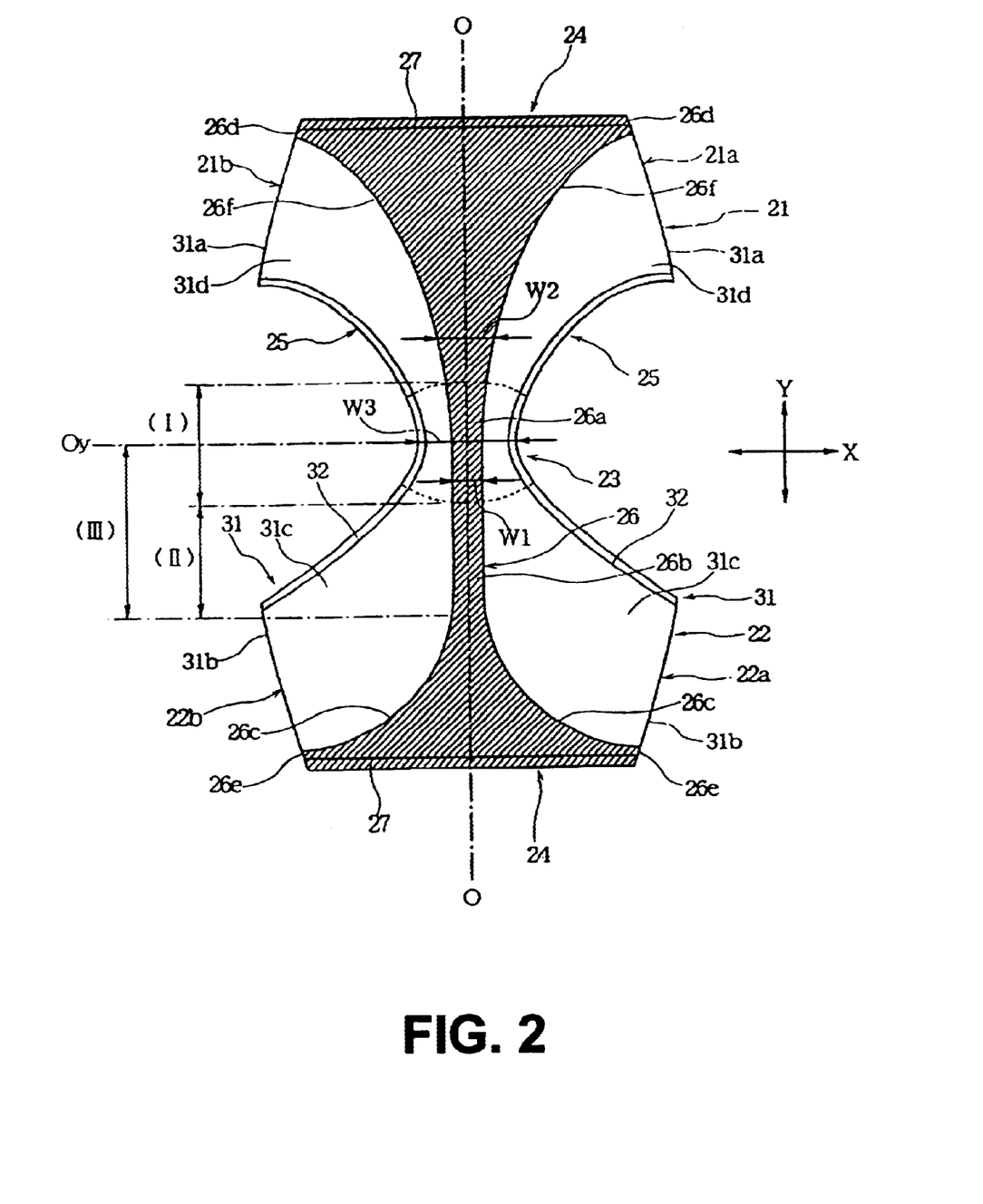
FIG. 2 is a development elevation of the sanitary panty of FIGS. 1A and 1B.

FIGS. 1A and 1B show the first embodiment of a sanitary panty according to the present invention, in which FIG. 1A is a front elevation and FIG. 1B is a back elevation, and FIG. 2 is a development elevation thereof.

The sanitary panty shown in FIGS. 1A, 1B and 2 is generally formed with a front part 21, a back part 22 and a crotch part 23.

In FIGS. 1A, 1B and 2, Y direction along which the front part 21, the crotch part 23 and the back part 22 are formed in series is referred to as longitudinal direction, and X direction transverse to the Y direction is referred to as lateral direction. A center line extending in the longitudinal direction at a center in the lateral direction is taken as O—O.

In FIG. 2, a side edge 21a of the front part 21 and a side edge 22a of the back part 22 are sewn and a side edge 21b of the front part 21 and a side edge 22b of the back part 22 are sewn to form a sanitary panty having a waist portion 24 and leg openings 25.

In the central region of the sanitary panty in the lateral direction, a suspending member 26 is provided. The suspending member 26 is formed with a highly elastic material, such as stretch non-woven fabric, stretch woven fabric, in which an elastic thread, such as rubber thread, is interworked, or a breathing rubber sheet having a plurality of holes.

The suspending member 26 is formed with a narrow width portion 26a at the crotch part 23. The narrow width portion 26a has a width W1 in a range of greater than or equal to 10 mm and less than or equal to 40 mm, and more preferably greater than or equal to 20 mm and less than or equal to 40 mm. The narrow width portion 26a is formed in a crotch region (I) which extends from a lowermost end Oy of the crotch part 23 of the sanitary panty, frontwardly and rearwardly in a length greater than or equal to 50 mm. At a boundary region (II) between the crotch part 23 and a mid portion of the back part 22, the suspending member 26 forms a narrow width portion 26b in a range of the width W1, that is, in a range of greater than or equal to 10 mm and less than or equal to 40 mm, and more preferably greater than or equal to 20 mm and less than or equal to 40 mm.

The width of the narrow width portions 26a and 26b in the regions (I) and (II) may be constant or, varying within the foregoing value range of the width W1.

In the back part 22, from the boundary region (II) to the waist portion 24, the suspending member 26 is formed with concave curved edge portions 26c to gradually increase the width of the suspending member 26 in X direction. In the waist portion 24 of the back part 22 (back portion of the waist portion), the width of the suspending member 26 matches with the overall length in the width in the X direction of the waist portion 24.

The preferred height (III) of the boundary region (II) (i.e., the height (III) indicates a range from the lowermost end Oy to the upper end of the boundary region (II)) where the width of the suspending member 26 becomes W1, assuming that the height from the lowermost end Oy of the sanitary panty in the three dimensional shape as worn on the wearer's body is H, is preferably less than or equal to four fifth and greater than or equal to one fourth of the overall height H, as shown in FIG. 1B.

The width W1 is set to be smaller than a width of the sanitary napkin. Since the width of the body portion (portion excluding wings) of the sanitary napkin is typically in a range of 40 to 70 mm. Therefore, the width W1 of the narrow width portion 26a of the suspending member 26 positioned at the crotch part 23 is preferred to be in a range of 10 to 40 mm.

Since the width of the narrow width portion 26b of the suspending member 26 in the boundary region (II) from the crotch part 23 to the back part 22 is in the range of the width W1, and the height (III) of the boundary region (II) is less than or equal to four fifth and greater than or equal to one fourth of the overall height H, the narrow width portion 26b may located in a rump-cleft, when the sanitary panty is worn.

In the front part 21, from the position where the suspending member 26 exceeds the region (I) of the crotch part 23, the width of the suspending member 26 is gradually increased to define concave curved edge portions 26f. In the waist portion 24 of the front part 21 (front portion of the waist portion), the width of the suspending member 26 matches with the overall length in the width in the X direction of the waist portion 24. As shown in FIGS. 1A and 1B, in the front part 21 opposing to the portion where the width of the suspending member 26 in the back part 22 is W1, the width W2 of the suspending member 26 is greater than W1.

Since the width W2 of the suspending member 26 in the front part 21 is wider than the width W1 of the suspending member 26 in the back part 22, local pressure feeling will be averted on the pubis portion and the inferior belly portion as worn.

As shown in FIG. 2, in the waist portion 24 of the front part 21, edge portions 26d of the suspending member 26 match with the side edges 21a and 21b of the front part 21. Similarly, in the waist portion 24 of the back part 22, edge portions 26e of the suspending member 26 match with the side edges 22a and 22b of the back part 22. Therefore, as shown in FIG. 1, when the sanitary panty is sewn, the edge portions 26d and 26e are connected. Thus, the entire circumference of the waist portion 24 is formed with the same material as the suspending member 26.

Furthermore, in the waist portion 24, an elastic member 27 is fitted over the entire circumference. Thus, a waist band elastically contacting with the wearer's body is formed over the entire circumference in the waist portion 24.

In the sanitary panty shown in FIGS. 1A, 1B and 2, extension cloths 31 are provided at both sides of the suspending member 26. The extension cloths 31 and the suspending member 26 may be sewn with each other at boundaries. In the alternative, it is also possible to form the entire panty with the cloth forming the extension cloths and sew the suspending member 26 at the central portion thereof in overlapping manner.

The extension cloth 31 is formed with woven fabric or non-woven fabric and has little stretchability. In the alternative, the material of the suspending member 26 and the material of the extension cloth 31 are formed into the equal width and, the material of the suspending member 26 and the material of the extension cloth 31 are selected so that, when the same tension force is applied, the stretching amount of the material of the suspending member 26 is greater than the material of the extension cloth 31. In the further alternative, the extension cloth 31 may be a stretchable material, and the material of the suspending member 26 and the material of the extension cloth 31 are given in the same width. In such case, the material of the suspending member 26 and the material of the extension cloth 31 are selected so that, when the suspending member 26 and the extension cloth 31 are stretched in the same amount, the material of the suspending member 26 has greater contraction stress than that of the material of the extension cloth 31.

In the embodiment shown in FIGS. 1A, 1B and 2, the extension cloth 31 is provided over the entire region of the front part 21, the back part 22 and the crotch part 23. In the front part 21, both end portions 31a of the extension cloths 31 match with the side edges 21a and 21b of the front part 21, and the other hand, in the back part 22, both end portions 31b of the extension cloths 31 match with both side edges 22a and 22b.

Accordingly, in the sewn condition of the sanitary panty as shown in FIGS. 1A and 1B, both end portions 31a of the extension cloth 31 are sewn with the both ends 31b to define leg openings 25 in the lower side of the sewn portion. Namely, the entire circumferences of the leg openings 25 are formed with the material of the extension cloth 31. On the other hand, on the circumferential edge portions of the leg openings 25, elastic members 32 are provided over the entire circumference to form leg fitting bands.

In the crotch part 23, the width W3 including the suspending member 26 and the extension cloths 31 substantially matches with the width of the body portion of the sanitary napkin, and preferably in a range greater than or equal to 30 mm and less than or equal to 70 mm. In the crotch part 23, a waterproof sheet 33 having stretchability and moisture permeability is fitted on inside.

On the other hand, by the extension cloth 31 extending from the crotch part 23 to the back part 22, a hip receiving portion 31c is formed. The extension cloth extending from the crotch part 23 to the front part 21 forms an inferior belly receiving region 31d.

The sanitary napkin shown in FIGS. 1A, 1B and 2 is worn in the condition where the sanitary napkin with the winds or the like is fitted inside of the crotch part 23. In the worn condition, since the suspending member 2 formed with the stretchable material is provided over the front part 21, the crotch part 23 and the back part 22, the sanitary napkin fitted inside of the crotch part 23 is elastically biased by the suspending member 26 to be firmly fitted to the wearer's body.

Here, in the crotch part 23, since the narrow width portion 26a of the suspending member 26 is provided the width W1 narrower than the width of the body portion of the sanitary napkin, the sanitary napkin is urged toward the wearer's body at greater force at the center portion in the width direction of the sanitary napkin. Namely, the sanitary napkin is urged onto the wearer's body in the convex condition toward the wearer's body. Therefore, the body portion of the sanitary napkin can be assured firm fitting to the wearer's body. On the other hand, in the crotch part 23, the extension cloths 31 extend from both sides of the narrow width portion 26a of the suspending member 26. Since the extension cloths 31 are formed with the material having lower stretchability than the suspending member 26 or having smaller elastic stress than the suspending member 26, the portion of the body portion of the sanitary napkin extending from the both sides of the suspending member 26 can be urged toward the wearer's body with smaller fitting force.

On the other hand, in the boundary region (II), the suspending member 26 is the narrow width portion 26b provided the width W1 so that the narrow width portion 26b may penetrate into the rump-cleft. By penetration of the narrow width portion 26b into the rump-cleft, in the crotch part, the narrow width portion 26a is hardly released from the crotch of the wearer's body. Thus, the sanitary napkin can be firmly fitted to the wearer's body at the center portion.

The sanitary napkin firmly fitted on the wear's body in the condition set forth above, hardly cause side disposition as the center portion is firmly fitted to the wearer's body in convex form (i.e., generally V-shaped cross-section). Therefore, leakage of menstrual blood can be hardly caused to successfully prevent side leakage of the menstrual blood to the sanitary panty.

On the other hand, as shown in FIG. 1B, in the back part 22, the curved edge portions 26c are formed in the suspending member 26 continuous with the narrow width portion 26b to gradually increase the width of the suspending member 26 toward the waist portion 24. On the other hand, in the front part 21, the curved edge portions 26f are provided in the suspending member 26 to gradually increase the width of the suspending member 26 toward the waist portion 24. Thus, the waist portion 24 is formed with the material of the suspending member 26 over the entire circumference.

In the front part 21 and the back part 22, particularly in the back part 22, the width of the suspending member 26 increases gradually to reach the waist portion 24. Therefore, the elastic stress of the suspending member 26 suspending the sanitary napkin does not locally concentrate in the waist portion 24 to be distributed over the entire length of the waist portion 24.

Accordingly, as in the prior art shown in FIGS. 5A and 5B, the waist portion 24 will never curved toward the crotch part locally to assure firm fitting of the waist portion 24 on the wearer's body. Namely, in the waist portion 24, the sanitary panty is firmly fitted on the waist portion of the wearer's body with the elastic contracting force of the elastic member 27 and elastic contracting force of the material forming the suspending member 26. At this time, in the left and right side portions of FIGS. 1A and 1B, the waist portion is hooked on the haunch bone to prevent slacking down. Also, the elastic stress of the suspending member 26 distributes over the entire length of the waist portion 24 in the back portion and the abdominal portion so that it prevents the sanitary panty from slacking down due to motion of the wearer's body while wearing.

Accordingly, the narrow width portion 26a of the suspending member 26 urging the sanitary napkin in the crotch part 23 may not be loosen to hardly cause disposition of the sanitary napkin fitted to the crotch of the wearer's body.

On the other hand, since the suspending member 26 is fitted from the crotch of the wearer's body to the rump-cleft and the upper hip portion to hardly form the crease in the portion of the suspending member 26. Also, the shown embodiment of the sanitary panty may provide superior wearing comfort.

Figure 3A:
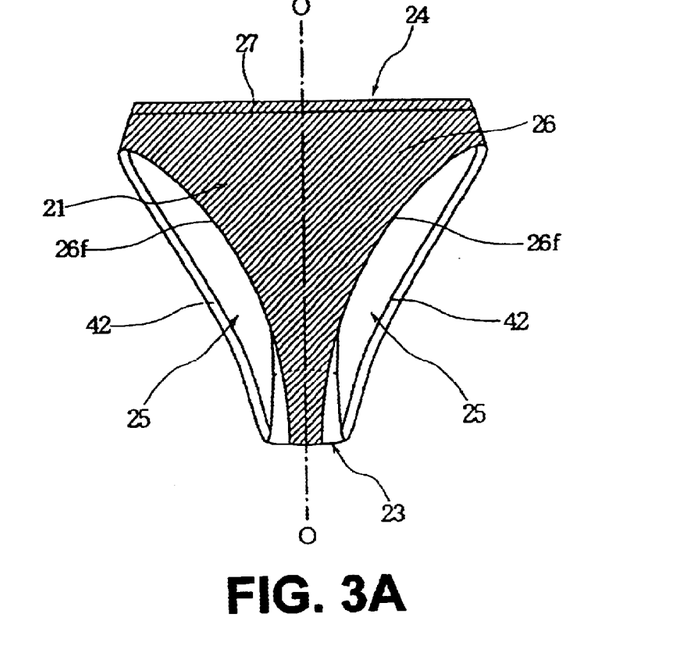
FIG. 3A is a front elevation and FIG. 3B is a back elevation.
Figure 3B:
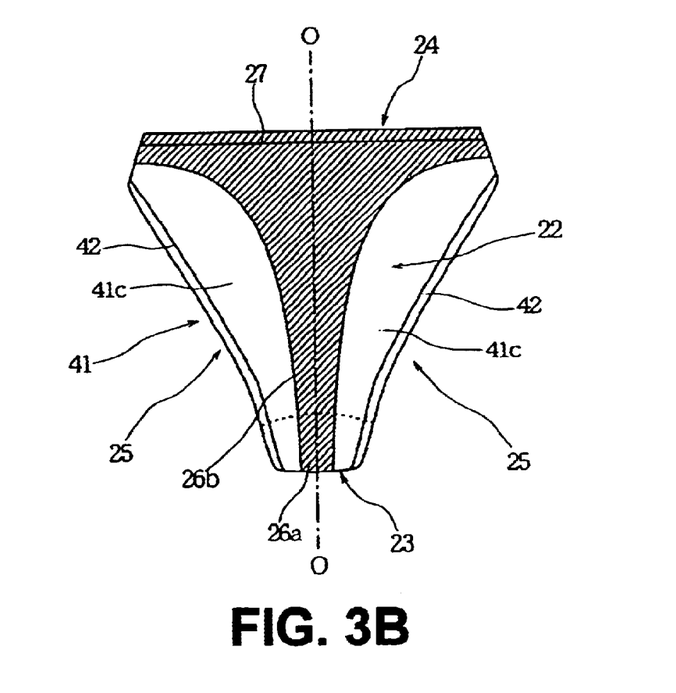
Figure 4:
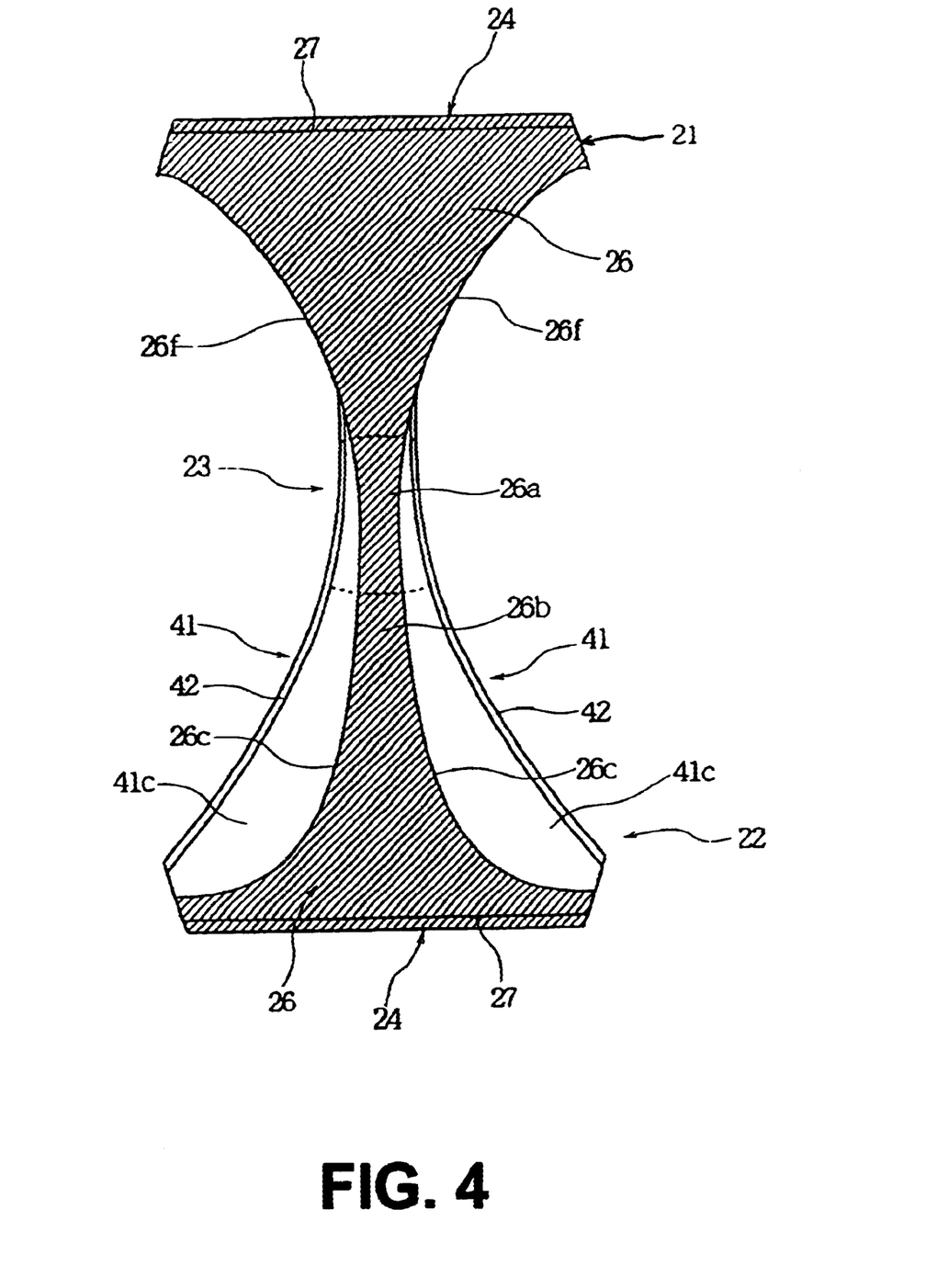
FIG. 4 is a development elevation of the sanitary panty of FIGS. 3A and 3B.

FIGS. 3A and 3B show the second embodiment of the sanitary panty according to the present invention, in which FIG. 3A is a front elevation and FIG. 3B is a back elevation, and FIG. 4 is a development elevation.

In the second embodiment of the sanitary panty shown in FIGS. 3A, 3B and 4, the suspending member 26 of substantially the same shape as that illustrated in FIGS. 1A, 1B and 2, is provided. The suspending member 26 is formed with the narrow width portion 26a of a width W1 in the crotch part 23. Also, in the boundary region from the crotch part 23 to the back part 22, the narrow width portion 26b of the width W1 is provided. Then, in the back part 22, the concave curved edge portions 26c continuous with the narrow width portion 26b are formed. The suspending member 26 gradually increases the width to reach the waist portion 24.

Furthermore, in the front part 21, the suspending member 26 has the curved edge portions 26f. The suspending member 26 gradually increases the width to reach the waist portion 24.

In the embodiment shown in FIGS. 3A, 3B and 4, extension cloths 41 formed with the same material as the extension cloth 31 in the former embodiment (as shown in FIGS. 1A and 1B) are provided. The extension cloths 41 extend from both side portions of the suspending member 26. In the shown embodiment illustrated in FIGS. 3A, 3B and 4, the extension cloths 41 are provided only in a region from both sides of the narrow width portion 26a to both sides of the suspending member 26 in the back part 22. In the front part 21, the extension cloth 41 is not provided.

As shown in FIGS. 3A and 3B, in the sewn condition of the sanitary panty, both ends in the width direction of the suspending member 26 located at the front part 21 are connected with both ends in the width direction of the suspending member 26 located at the back part 22 to form the waist portion 24 with the material of the suspending member 26 in the entire circumference.

In the crotch part 23, the entire width of the suspending member 26 and the extension cloths 41 is W3 similarly to FIG. 2. On the other hand, in the back part 22, the extension cloths 41 form hip receiving portions 41c.

The sanitary panty shown in FIGS. 3A, 3B and 4 serves the same function as the sanitary panty shown in FIGS. 1A, 1B and 2 to assure firm fitting of the sanitary napkin set in the crotch part 23 onto the wearer's body. Also, the elastic stress of the suspending member 26 is distributed over the entire length of the waist portion 24 so as not to cause slacking down or to form the crease to assure firm fitting.

It should be noted that, as shown in FIG. 4, elastic member 42 may be provided on the edge portion of the extension cloths 41 to form fitting band for firm fitting of the leg opening 25 to the wearer's legs.

As set forth above, the sanitary panty according to the present invention, the extension cloths 31 may be provided over all regions of the front part 21, the crotch part 23 and the back part 22, or in the alternative, the extension cloths 41 may be provided only in the crotch part 23 and the back part 22. In the further alternative, the extension cloths may be provided only in the crotch part 23 to extend from both sides of the narrow width portion 26a of the suspending member 26, without providing the extension cloths for forming the hip receiving portions in the back part 22.

As set forth above, the sanitary panty according to the present invention deforms the sanitary napkin in convex form to be constantly fitted on the wearer's body to prevent menstrual blood from leaking. Also, by distributing the elastic stress of the suspending member in the waist portion, slacking down of the sanitary napkin can be prevented. Therefore, the force urging the sanitary napkin onto the wearer's body will never be relaxed and the crease is hardly formed.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A sanitary panty for fitting and maintaining a sanitary napkin on a crotch area of a wearer comprising:
   a front part;
   a back part;
   a crotch part positioned between said front part and said back part;
   a waist portion formed by upper end portions of said front part and said back part;
   a pair of leg opening formed below joining portions between side edges of said front part and side edges of said back part;
   a suspending member extending from said front part, said crotch part and said back part, having a width W1 greater than or equal to 10 mm and less than or equal to 40 mm in said crotch part and substantially half of said back part extending from a rear end of said crotch part and formed with a stretchable material for elastically biasing said sanitary napkin onto said crotch area of said wearer when worn, said suspending member being gradually reduced in width from said waist portion to said crotch part in said back part; and
   an extension clothe tending from both sides of said suspending member to said leg openings at least in said crotch part.

2. A sanitary panty as set forth in claim 1, wherein a narrow width portion in which a width falls within a range of the width W1, is provided in said suspending member from said crotch part to a given height position of said back part.

3. A sanitary panty as set forth in claim 1, wherein both side portions of said suspending member located in said front part are connected to both side portions of said suspending member located in said back part to form said waist portion with said stretchable material forming said suspending member.

4. A sanitary panty as set forth in claim 1, wherein said extension cloth is provided from said crotch part to said back part to form a hip receiving portion.

5. A sanitary panty as set forth in claim 1, wherein said extension cloth is further extended from both sides of said suspending member in said front part, both end portions of said extension cloth located in said front part and both end portions of said extension cloth located in said back part are connected to form the entire circumference of said leg openings with a material of said extension cloth.

6. A sanitary panty as set forth in claim 1, wherein the material forming said extension cloth is not stretchable or has smaller stretching amount than that of said suspending member when the same tension force is applied.

7. A sanitary panty as set forth in claim 6, wherein the material forming said extension cloth has stretchability and has an elastic stress smaller than that of said stretchable material forming said suspending member when said extension cloth and said suspending member are stretched in the same amount.

8. A sanitary panty as set forth in claim 1, wherein a waterproof sheet having stretchability and moisture permeability is fitted inside of said crotch part or a portion extending from said crotch part to said back part.

9. A sanitary panty for fitting and maintaining a sanitary napkin on a crotch area of a wearer, comprising:
   a front part;
   a back part;
   a crotch part positioned between said front part and said back part;
   a waist portion formed by upper end portions of said front part and said back part;
   a pair of leg opening formed below joining portions between side edges of said front part and side edges of said back part;
   a suspending member formed with a stretchable material and extending from said front part, said crotch part an said back part for elastically biasing said sanitary napkin onto said crotch area of said wearer when worn, said suspending member being gradually reduced in width from said waist portion to said crotch part in said back part; and
   an extension cloth tending from both sides of said suspending member to said leg openings at least in said crotch part;
   wherein said front art is formed only by the material forming said suspending member.

10. A sanitary panty for fitting and maintaining a sanitary napkin on a crotch area of a wearer, comprising:
    a front part;
    a back part;
    a crotch part positioned between said front part and said back part;
    a waist portion formed by upper end portions of said front part and said back part;
    a pair of leg openings formed below joining portions between side edges of said front part and side edges of said back part;
    a suspending member integrally formed with a non woven stretchable material for elastically urging said sanitary napkin onto said crotch area of said wearer when worn, and extending from said front art, said crotch part and said back part, said suspending member being gradually reduced in width from said waist portion to said crotch part in said back part; and
    an extension clothed tending from both sides of said suspending member to said leg openings at least in said crotch part.

11. A sanitary panty for fitting and maintaining a sanitary napkin on a crotch area of a wearer comprising:
    a front part;
    a back part;
    a crotch part positioned between said front part and said back part;
    a waist portion formed by upper end portions of said front part and said back part;
    a pair of leg openings formed below joining portions between side edges of said front part and side edges of said back part;

a suspending member integrally formed with a stretch woven fabric in which an elastic thread is interworked or elastically urging said sanitary napkin onto said crotch area of said wearer when worn, and extending from said front part, said crotch part and said back part, said suspending member being gradually reduced in width from said waist portion to said crotch part in said back part; and an extension cloth extending from both sides of said suspending member to said leg openings at least in said crotch part.

12. A sanitary pant as set forth in claim 11, wherein said elastic thread is a rubber thread.

13. A sanitary panty for fitting and maintaining a sanitary napkin on a crotch area of a wearer comprising:

a front part;

a back part;

a crotch part positioned between said front part and said back part; a waist portion formed by upper end portions of said front part and said back part;

a pair of leg openings formed below joining portions between side edges of said front part and side edges of said back part;

a suspending member integrally formed with a breathing rubber sheet for elastically urging said sanitary napkin onto said crotch area of said wearer when worn having a plurality of holes and extending from said front part, said crotch part and said back part, said suspending member being gradually reduced in width from said waist portion to said crotch part in said back part; and an extension clothe tending from both sides of said suspending member to said leg openings at least in said crotch part.

14. A sanitary panty for fitting and maintaining a sanitary napkin on a crotch area of a wearer, comprising:

a front part;

a back part;

a crotch part positioned between said front part and said back part;

a waist portion formed by upper end portions of said front part and said back part;

a pair of leg openings formed below joining portions between side edges of said front part and side edges of said back part;

a suspension member formed with a stretchable material and extending from said front part, said crotch part and said back part for elastically biasing said sanitary napkin onto said crotch area of said wearer when worn, said suspending member being gradually reduced in width from said waist portion to said crotch part in said back part; and an extension cloth extending from both sides of said suspending member to said leg openings at least in said crotch part.

* * * * *